United States Patent [19]

Johnson

[11] Patent Number: 4,625,552

[45] Date of Patent: Dec. 2, 1986

[54] INSTRUMENT FOR SEPARATING FLUFF COMPONENTS

[75] Inventor: Carl W. Johnson, Neenah, Wis.

[73] Assignee: Specialty Research, Inc., Neenah, Wis.

[21] Appl. No.: 791,307

[22] Filed: Oct. 25, 1985

[51] Int. Cl.[4] ............................................ G01D 21/00
[52] U.S. Cl. ..................................... 73/865.5; 73/866
[58] Field of Search ............. 73/432 Z, 432 R, 432 PS

[56] References Cited

U.S. PATENT DOCUMENTS

| | | | |
|---|---|---|---|
| 3,636,772 | 1/1972 | Bennett | 73/432 Z |
| 3,813,947 | 6/1974 | Hinde | 73/432 PS |
| 4,154,111 | 5/1979 | Anderson et al. | 73/432 PS |

FOREIGN PATENT DOCUMENTS

| | | | |
|---|---|---|---|
| 215581 | 5/1968 | U.S.S.R. | 73/432 PS |
| 214197 | 6/1968 | U.S.S.R. | 73/432 Z |
| 308354 | 8/1971 | U.S.S.R. | 73/432 PS |
| 421916 | 9/1974 | U.S.S.R. | 73/432 PS |

OTHER PUBLICATIONS

"The Profitable Use of Testing Sieves", Catalog 48 of The W. S. Tyler Company; cover, pp. 21-23 Sieve Test-Ro-Tap Method, and pp. 50-51 Ro-Tap Testing Sieve Shaker; 1926.

"Particle Size Analysis by Automatic Siever"; Powder Technology 24, No. 2, Dec. 1979; pp. 143-149, C. Orr et al.

Primary Examiner—Michael J. Tokar
Assistant Examiner—Tom Noland
Attorney, Agent, or Firm—Nicholas A. Kees

[57] ABSTRACT

An instrument for separating out any one or more of the components of any given sample of fluff. The instrument includes a base having an annular opening formed in its upper surface. A spindle is journaled in the base, and supports a sieve and enclosure over itself. A compressed air bar is located between the sieve and the spindle, to allow compressed air to escape through the sieve and impact on the fluff sample in the enclosure. A motor is provided to turn the chamber, sieve and enclosure while the air bar is held stationary. The motor turns the spindle by any suitable arrangement such as belt drive, rim drive, direct drive or any other appropriate arrangement. A vacuum motor and assembly communicates with the annular base opening to draw components to be separated from the sample through the sieve, spindle and base, leaving only the remaining components in the enclosure above the sieve. These components are compared to determine the quality of the fluff sample.

14 Claims, 3 Drawing Figures

INSTRUMENT FOR SEPARATING FLUFF COMPONENTS

BACKGROUND OF THE INVENTION

This invention relates to test instruments, and in particular to instruments for automatically separating out any one or more of the components of fluff in order to establish and measure the quality of the fluff.

Absorbent products such as disposable diapers and feminine hygiene pads are conventionally manufactured around pads made of "fluff". Fluff is a collection of wood pulp fibers which may be formed into a pad shape, depending upon the particular intended use, by suitable apparatus. If it is recycled fluff, it also may include bits of reclamation waste, such as plastic or other materials from the fluff-based items being recycled. The fluff with the greatest absorbency is the fluff which is most highly fiberized, that is, the fluff in which the greatest number of fibers are separated from each other without breaking the fibers into smaller pieces, called "fines". If the fibers are broken into smaller pieces the absorbency is reduced. If the fluff is not completely fiberized, the remaining bits of wood pulp are called "knots", and again the absorbency of the produced pad is lowered. "Fiberization percentage" is the percent by weight of a particular sample of fluff which is fiberized, the remainder consisting of knots, fines and possibly reclamation waste. That is, the fiberization percentage is arrived at by separating the fluff fibers from the other components in a particular sample of pad, and dividing the weight of the fibers by the weight of the total sample.

There are a number of companies that offer the service of testing fluff to determine the fiberization percentage. Several such companies offer these services as an adjunct to their main business of selling pulp to the papermaking and paper converting industries. One such company is Buckeye Cellulose Corporation of Memphis, Tenn. The apparatus used by this company for conducting this testing consists of a chamber to which a vacuum is applied. An ASME testing sieve of a predetermined mesh is placed over the chamber. A sample of fluff is placed on the sieve. The sample is agitated by use of a compressed air hose. The operator uses the air from the hose to agitate the sample until only the knots remain above the sieve. The knots are recovered and weighed to determine the complement of the fiberization percentage or, as that company calls it, the disintegration percentage.

The problem with this method and apparatus is that there is a great deal of hand work involved in the testing. This type of testing is therefore not easily reproducible, and several tests conducted on samples taken from the same collection of fluff can result in widely differing test statistics if the operator is not highly skilled. In addition, there is demand for an apparatus which can separate out any one or more of the components of the fluff.

The invention relates to improvements over the apparatus discussed above and to solutions to the problems raised thereby.

SUMMARY OF THE INVENTION

In the description following, reference is made to the removal of fluff fibers and fines from a sample. This specific example is used for clarity and illustration only, and is not intended to be limiting. In all, the invention encompasses the removal of any one or more of the components of a particular fluff sample, whether those components be knots, fibers, fines or reclamation waste.

The invention includes two chambers, a knot chamber and a fiber transport chamber, separated by a conventional ASME testing sieve contained within the floor of the knot chamber. The size of the openings of the sieve are predetermined in order to allow the passage of individual pulp fibers but prevent the passage of knots, or at least the great majority of the knots. A vacuum is applied to both chambers by means of a single vacuum source. A source of compressed air is located below the sieve in the fiber transport chamber, allowing the compressed air to blow through the sieve, into the knot chamber. A sample of fluff is placed in the knot chamber, and the knot chamber is caused to rotate with respect to the compressed air bar. The sample is thus agitated by compressed air, and the loose fibers are separated from the sample, to be drawn through the sieve by the vacuum, while the knots are left in the knot chamber. The fibers are caught in a finer sieve before they reach the vacuum motor. The fines are allowed to pass through the vacuum source and are caught in a filter.

It is thus an object of the invention to provide an apparatus for automatically separating components of a fluff sample in a reproducible and reliable manner.

A more specific object of the invention is to provide an apparatus as described above having a knot chamber and a fiber transport chamber, along with a pneumatic device to automatically agitate a sample of pulp fluff in the knot chamber so that the loose fibers can be removed to the fiber transport chamber by vacuum, leaving the knots behind.

Another specific object of the invention is to provide an apparatus as recited above wherein the knot chamber is automatically rotated with respect to the agitating device, to further improve agitation of the sample.

Other objects and advantages of the invention will become apparent hereinafter.

DESCRIPTION OF THE PREFERRED EMBODIMENTS

Figure 1:
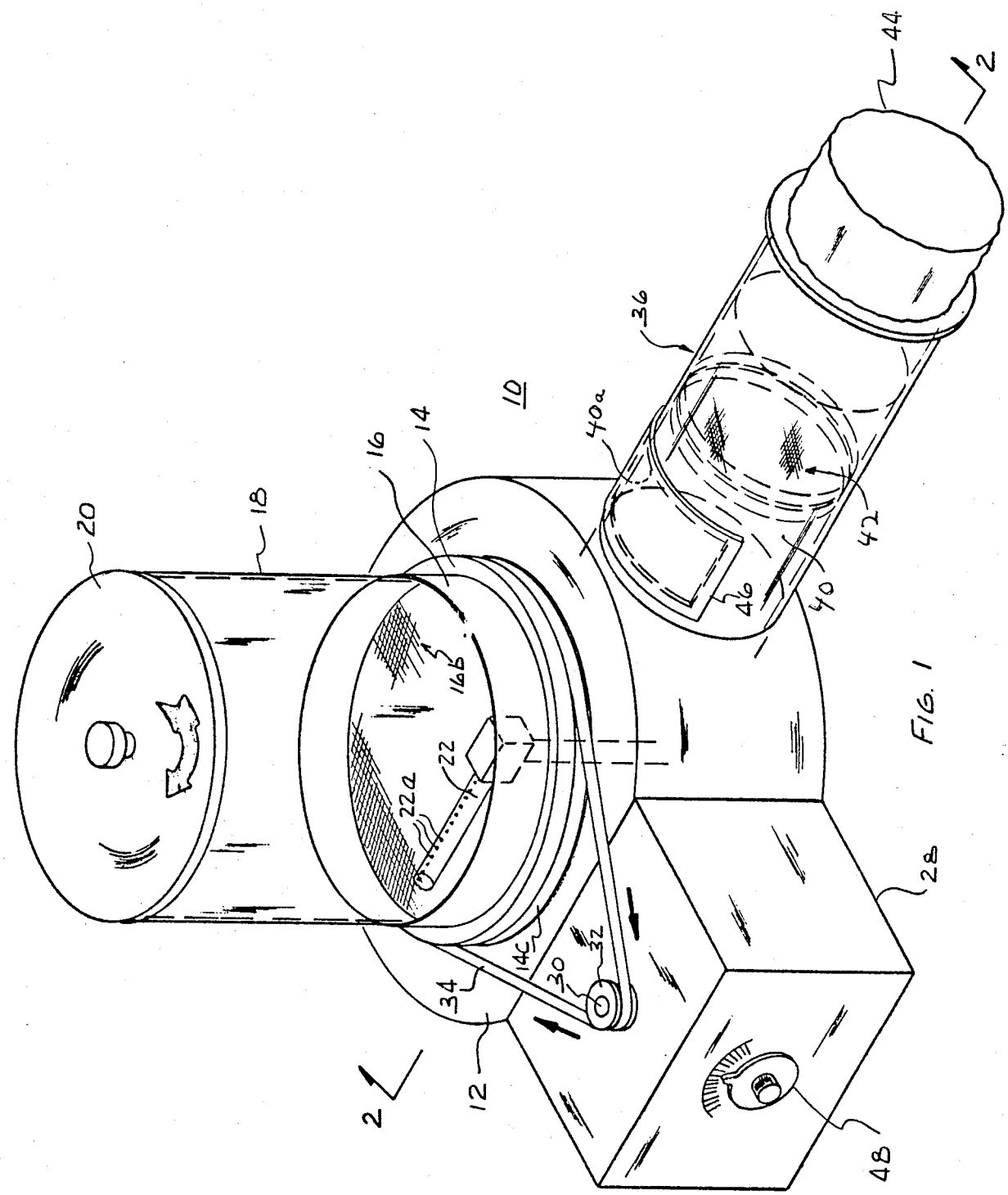
FIG. 1 is an isometric view of one embodiment of the invention.

Referring now to the drawing figures, the testing apparatus is designated generally at 10. The spatial orientation of apparatus 10 is not necessarily important. However, for clarity of explanation only, the following description does include words such as "upper," "lower," "left," and "right" in referring to the drawing figures. These words are not intended to limit the scope of the invention.

Figure 3:
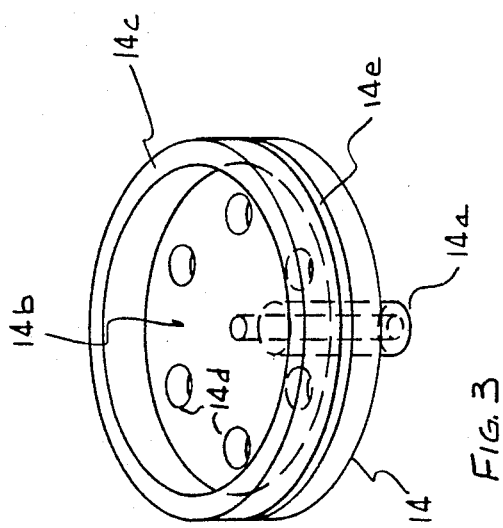
FIG. 3 is an isometric view of the spindle with its hub enlarged to accommodate the screen.
Figure 2:
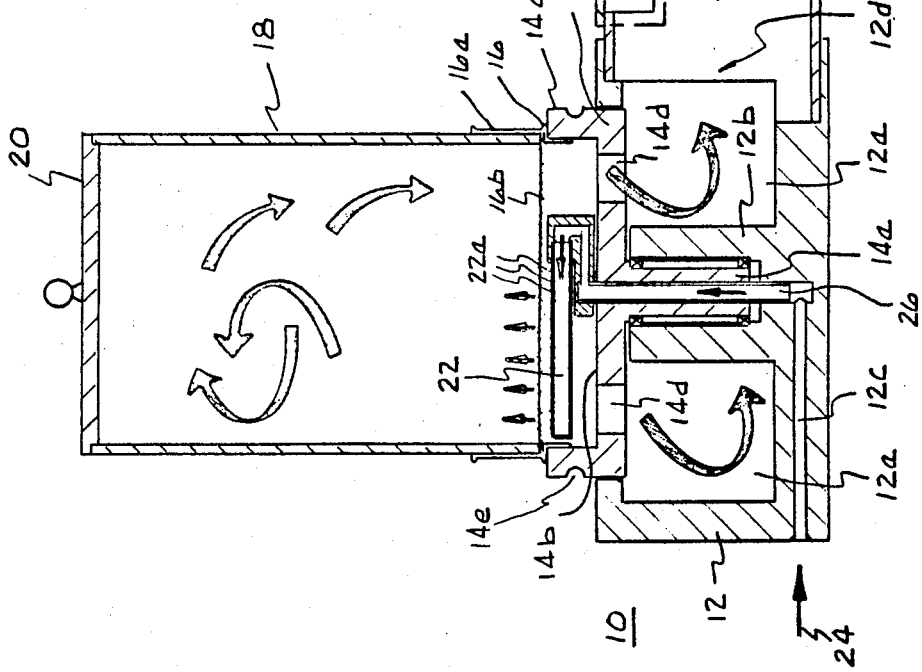
FIG. 2 is a sectional view of the embodiment shown in FIG. 1, along line 2—2.

As shown in the figures, the apparatus 10 includes a base portion 12 for support. Base 12 includes a large annular opening 12a in its upper surface, with a hub portion 12b in the center (FIG. 2). Hub 12b is hollowed out vertically at its center to accept the stem 14a of a spindle 14. Stem 14a is journaled inside hub 12b. Besides stem 14a, spindle 14 (also shown in isometric in FIG. 3) preferably includes a flat upper surface 14b at the top of stem 14a, an upstanding rim 14c at the outside edge of surface 14b, and at least one and preferably several openings 14d in the surface 14b, allowing the area above surface 14b to communicate with the annular opening 12a below. An ASME testing sieve assembly 16 rests on and preferably pilots partially into rim 14c. Sieve assembly 16 includes an annular sieve rim 16a and the sieve screen 16b itself secured inside the rim 16a. Resting on and preferably piloting partly into sieve assembly 16 is an enclosure 18, preferably having a cover 20 or other opening device, which may be located at the top. It is advantageous for this enclosure 18 to be made of transparent material, such as Lexan or Plexyglass, so that the operator can view the sample and monitor the progress of the test. A pneumatic agitation air bar 22 is located between the spindle 14 and sieve 16b. The bar 22 has a plurality of openings 22a in its upper surface, extending radially from one edge of sieve 16b to at least beyond the center thereof. Bar 22 is connected to a source of compressed air (not shown) indicated by arrow 24. The air follows an opening 12c formed integrally in base 12 and continues through a pipe 26 rigidly connected to opening 12c. Pipe 26 extends upward through the center of stem 14a of the spindle 14 and connects to horizontal air bar 22. Because air bar 22 and pipe 26 are rigidly attached to base 12, they do not rotate with spindle 14 as it turns. Rather, they are held stationary so that bar 22 passes under all parts of sieve 16b as it rotates with spindle 14, so that any fluff sample in the knot chamber formed by enclosure 18 and sieve 16 is continually and completely agitated.

As described above, spindle 14 is journaled in base 12. As shown in FIG. 1, spindle 14 and consequently sieve 16 and enclosure 18, are caused to move with respect to air bar 22 during a test. The movement shown is rotation, but any other repetitive type of relative movement is included. This movement is accomplished by any suitable drive means. The drive means shown in FIG. 1 is a motor (not shown) located inside a control enclosure 28 and connected by a shaft 30, which extends outside of the enclosure 28, to a pulley 32. Pulley 32 then drives a belt 34 which passes around rim 14c of spindle 14, preferably in a groove 14e thereof. Any other means for continually rotating spindle 14 could also be employed just as advantageously, such as a rim drive arrangement where a motor drives a wheel (not shown) bearing directly on the rim 14c of the spindle 14 or a direct drive arrangement where a motor is directly connected to the spindle 14 to rotate it.

Referring again to FIG. 2, annular opening 12a has a outlet 12d which communicates with a vacuum assembly 36. The purpose of vacuum assembly 36 is to draw the loose fluff fibers from the sample through sieve 16b and out of base 12. The vacuum assembly 36 is mostly elongated in shape, one end being connected to opening 12d in base 12. The assembly includes a motor 38 for powering a blower (not shown) which in turn draws the fluff fibers and air out as described above. The assembly also includes a fiber chamber 40 located between the base 12 and the motor 38, and separated from the motor by a catch sieve 42. Clearly, catch sieve 42 must be substantially finer than sieve 16b so that substantially all of the fibers are caught therein. At the distal end of vacuum assembly 36, beyond vacuum motor 38, there is located a dust filter bag 44 so that any dust particles which do pass through catch sieve 42 are not passed out into the air. A door 46 is provided to cover an opening 40a in fiber chamber 40. Opening 40a is provided so as to allow easy access to and removal of fiber buildup on catch sieve 42.

Referring again to FIG. 1, some means is needed to control the apparatus and turn the motors and compressed air on and off. While the invention includes any suitable means, the means shown in FIG. 1 is a timer mechanism 48, located on enclosure 28. When timer 48 is turned on, both the motor connected to shaft 30 and the vacuum motor 38, along with the compressed air, is turned on. When the timer 48 runs out, all three are turned off. This gives the operator the capability of setting the timer and allowing the apparatus 10 to run unattended for a predetermined length of time. Alternatively, he can interrupt the operation at any time, such as by setting the timer to zero.

While the apparatus hereinbefore described is effectively adapted to fulfill the aforesaid objects, it is to be understood that the invention is not intended to be limited to the particular preferred embodiments of fluff testing apparatus herein set forth. Rather, the invention is to be taken as including various equivalents without departing from the scope of the appended claims.

What is claimed is:

1. An apparatus for testing for the amount of fiberization of a particular sample of fluff, comprising:
   a base for providing support and having an opening in its upper surface;
   a spindle journaled to said base and having at least one opening for communicating with the opening in said base;
   a testing sieve supported by said spindle and disposed on the opposite side of said spindle from said base, the openings of said sieve being sufficiently large to pass the great majority of fibers and sufficiently small to prevent the passage of the great majority of knots;
   an enclosure placed over said sieve;
   a compressed air bar communicating with a source of compressed air, disposed between said sieve and said spindle, for releasing compressed air through said sieve to impact on the sample;
   a vacuum means for drawing the fibers through said sieve, said spindle and said base; and
   means for automatically and continually rotating said spindle and sieve with respect to said air bar, so that the sample is continually and automatically agitated.

2. An apparatus as recited in claim 1 further comprising timer means for controlling said turning means and allowing an operator to cause the apparatus to run unattended for a predetermined length of time or to interrupt the operation of the apparatus at his discretion.

3. An apparatus as recited in claim 1 wherein said vacuum means includes an enclosure communicating with the opening of said base, a vacuum motor, a dust filter disposed beyond the vacuum motor, and a catch sieve, the mesh of which is fine enough to catch the great majority of loose fibers before they reach said vacuum motor.

4. An apparatus as recited in claim 3 further comprising means for opening said vacuum means enclosure to allow removal of fiber buildup on said catch sieve.

5. An apparatus as recited in claim 1 wherein said turning means includes a motor connected to said spindle by a belt drive arrangement.

6. An apparatus as recited in claim 1 wherein said turning means includes a motor driving a wheel which bears directly on a rim of said spindle in a rim drive arrangement.

7. An apparatus as recited in claim 1 wherein said turning means includes a motor connected directly to said spindle in a direct drive arrangement.

8. An apparatus for separating out at least one of the components of a particular sample of fluff, comprising:
- a base for providing support and having an opening in its upper surface;
- a spindle journaled to said base and having at least one opening for communicating with the opening in said base;
- a testing sieve supported by said spindle and disposed on the opposite side of said spindle from said base, the openings of said sieve being sufficiently large to pass the great majority of components to be separated out and sufficiently small to prevent the passage of the great majority of the components not to be separated out;
- an enclosure placed over said sieve;
- a compressed air bar communicating with a source of compressed air, disposed between said sieve and said spindle, for releasing compressed air through said sieve to impact on the sample;
- a vacuum means for drawing the components to be separated out through said sieve, said spindle and said base; and
- means for automatically and continually rotating said spindle and sieve with respect to said air bar, so that the sample is continually and automatically agitated.

9. An apparatus as recited in claim 8 further comprising timer means for controlling said turning means and allowing an operator to cause the apparatus to run unattended for a predetermined length of time or to interrupt the operation of the apparatus at his discretion.

10. An apparatus as recited in claim 8 wherein said vacuum means includes an enclosure communicating with the opening of said base, a vacuum motor, a dust filter disposed beyond the vacuum motor, and a catch sieve, the mesh of which is fine enough to catch the great majority of loose components to be separated out before they reach said vacuum motor.

11. An apparatus as recited in claim 10 further comprising means for opening said vacuum means enclosure to allow removal of buildup of separated components on said catch sieve.

12. An apparatus as recited in claim 8 wherein said turning means includes a motor connected to said spindle by a belt drive arrangement.

13. An apparatus as recited in claim 8 wherein said turning means includes a motor driving a wheel which bears directly on a rim of said spindle in a rim drive arrangement.

14. An apparatus as recited in claim 8 wherein said turning means includes a motor connected directly to said spindle in a direct drive arrangement.

* * * * *